United States Patent [19]

Kelly

[11] 3,976,667

[45] Aug. 24, 1976

[54] STEFFIMYCINONE, 7-DEOXYSTEFFIMYCINONE AND DERIVATIVES

[75] Inventor: Robert C. Kelly, Kalamazoo, Mich.

[73] Assignee: The Upjohn Company, Kalamazoo, Mich.

[22] Filed: June 19, 1975

[21] Appl. No.: 588,298

[52] U.S. Cl............................... 260/365; 424/230; 424/301; 424/302; 424/304; 424/305; 424/308; 424/309; 424/311; 424/312; 424/314; 424/331; 536/17

[51] Int. Cl.².................. C07C 49/74; C07C 69/18; C07C 69/21; C07C 69/30; C07C 69/33; C07C 69/61; C07C 69/63; C07C 69/67; C07C 69/68; C07C 69/74; C07C 69/78; C07C 69/84; C07C 69/92; C07C 69/96; C07C 79/46; C07C 121/00

[58] Field of Search..................................... 260/365

[56] References Cited
UNITED STATES PATENTS

| | | | |
|---|---|---|---|
| 3,590,028 | 6/1971 | Arcomone et al. | 260/396 R |
| 3,665,018 | 5/1972 | Jolles | 260/365 |
| 3,721,684 | 3/1973 | Meyers | 260/365 |
| 3,803,124 | 4/1974 | Arcomone et al. | 260/396 R |

*Primary Examiner*—Vivian Garner
*Attorney, Agent, or Firm*—Roman Saliwanchik

[57] ABSTRACT

Antibiotic steffimycinone (U-25,055), produced by acid hydrolysis or methanolysis of antibiotic steffimycin (U-20,661), or steffimycin B, and 7-deoxysteffimycinone (U-25,920) produced by hydrogenolysis of steffimycin or steffimycin B (U-40,615). Steffimycinone is active against various microorganisms, for example, *Bacillus subtilis*, *Mycobacterium avium* and *Bacillus cereus*; 7-deoxysteffimycinone is active against *Sarcina lutea* and *Mycobacterium avium*. Thus, these antibiotics can be used to inhibit the growth of the above microorganisms in various environments.

4 Claims, No Drawings 3,976,667

STEFFIMYCINONE, 7-DEOXYSTEFFIMYCINONE AND DERIVATIVES

BACKGROUND OF THE INVENTION

The process for preparing the antibiotic steffimycin, and the description of its various biological properties, are disclosed in U.S. Pat. No. 3,309,273. The antibiotic at that time was known as steffisburgensimycin.

The process for preparing steffimycin B and its characterization are disclosed in U.S. Pat. No. 3,794,721.

The structures of steffimycin and steffimycin B can be shown as follows:

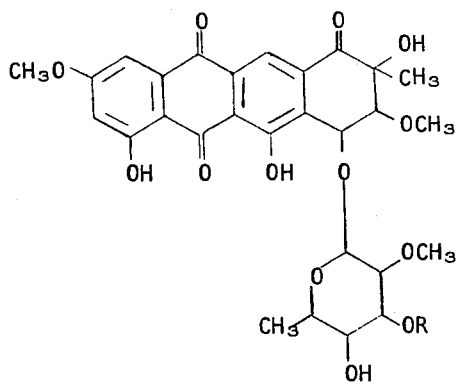

R = H (Steffimycin)
R = CH₃ (Steffimycin B)

BRIEF SUMMARY OF THE INVENTION

Steffimycinone can be prepared by acid hydrolysis of steffimycin or steffimycin B. 7-Deoxysteffimycinone can be prepared by hydrogenolysis, using a suitable catalyst, of steffimycin or steffimycin B. Both antibiotics are biologically active, as disclosed above, and can be used in various environments to inhibit the growth of susceptible microorganisms. For example, steffimycinone can be used for treating breeding places of silkworms, to prevent or minimize infections which are well known to be caused by *Bacillus subtilis*. Further, steffimycinone can be used in papermill operations to control the contamination of wool by the microorganism *Bacillus cereus*. 7-Deoxysteffimycinone can be used to control *Mycobacterium avium* which is a known producer of generalized tuberculosis in birds and rabbits.

DETAILED DESCRIPTION

Steffimycinone can be shown by the following structure:

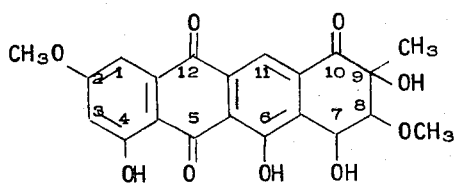

Steffimycinone can be prepared by acid hydrolysis of steffimycin or steffimycin B. The hydrolysis can be conducted with a mineral acid ranging from 0.1 to 3 N. Examples of acids which can be used are hydrochloric, sulfuric, and phosphoric.

The reaction can be conducted at a temperature of 0°C. to reflux. Reflux is preferred since lower temperatures prolong the completion of the reaction. The aglycon steffimycinone is recovered from the reaction mixture as crystals which form as the reaction is completed. Generally, crystals begin to appear after about 23 hours reaction time when the reaction is conducted at reflux.

7-Deoxysteffimycinone can be shown by the following structure:

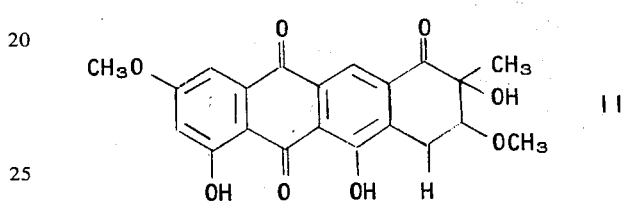

7-Deoxysteffimycinone can be prepared by hydrogenolysis using a suitable catalyst, for example, palladium, platinum, rhodium, or activated nickel. The reaction can be conducted at pressures ranging from atmospheric to 1000 psi. the lower the pressure, the longer the reaction time. A pressure of 45 to 50 psi is preferred.

Steffimycinone and 7-deoxysteffimycinone can be acylated under standard acylating conditions with an appropriate acid halide or anhydride to give the acylated compounds. Under these standard conditions, steffimycinone is acylated at the 4, 6 and 7 hydroxyls and 7-deoxysteffimycinone is acylated at the 4 and 6 hydroxyls. The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetec, valeric, isovaleric, caproic, caprylic, decanoic, dodecanoic, lauric, tridecanoic, myristic, pentadecanoic, plamitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and lower alkoxy- hydrocarbon carboxylic acids include hydrocarboncarboxylic acids as given above which are substituted by one or more of halogen, nitro, hydroxy, amino, cyano, or thiocyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcyclic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
and the like.

The acylated compounds, as described above, can be used in animals for the same biological purposes as disclosed above for steffimycinone and 7-deoxysteffimycinone. For example, the acylated compounds can be given in oral form to an animal possessing the necessary enzyme to remove the acyl group, thus freeing the parent antibiotic compound which then inhibits susceptible bacteria.

Steffimycinone and 7-deoxysteffimycinone form salts with alkali metals and alkaline earth metals. Metal salts can be prepared by dissolving steffimycinone or 7-deoxysteffimycinone in methanol, adding a dilute metal base until the pH of the solution is about 9 to 11, and freeze drying the solution to provide a dried residue consisting of the metal salt. Metal salts can be, for example, the sodium, potassium, and calcium salts.

Steffimycinone and 7-deoxysteffimycinone salts, as described above, can be used for the same antibacterial purposes as steffimycinone and 7-deoxysteffimycinone.

The following examples are illustrative of the process and products of the invention, but are not to be construed as limiting. All percentages are by weight and all solvent mixture proportions are by volume unless otherwise noted.

EXAMPLE 1

Steffimycinone — U-25,055.

5.0 g. of steffimycin is heated under reflux in 500 ml. of 1N methanolic hydrochloric acid. The course of the reaction is followed by spotting 2 μl aliquots on a silica gel TLC (thin layer chromatography) plate and developing with methanol-methylene chloride (5:95). Under these conditions, the steffimycinone has an Rf of 0.31 and steffimycin an Rf of 0.12. After 23 hours, steffimycinone begins to crystallize out of the reaction mixture, and after 128 hours the reaction mixture is cooled even though a small amount of steffimycin is still detectable by TLC. The crystalline steffimycinone is collected and dried giving 2.84 g. of small orange prisms; m.p. 245°–253°. A second crop gives 0.5 g. of crystal; m.p. 228°–245°. These fractions are combined and crystallized from methanol giving 2.45 g. of crystals; m.p. 248°–250°. A second crop gives 0.74 g., m.p. 245°–249°. The total yield is 3.19 g. or 87%. A sample is prepared for analysis by two further crystallizations from methanol; m.p. 250°–251.5°.

|  | C | H |
|---|---|---|
| Found | 60.14 | 4.77 |
| Calcd. for $C_{21}H_{18}O_9 + \frac{1}{2}CH_3OH$ | 60.00 | 4.68 |

Infrared Absorption Spectra: (In a mineral oil mull). The following wave lengths are expressed in reciprocal centimeters: 3500, 3070W (weak), 1710, 1675, 1625, 1600, 1560, 1315, 1250, 1200, 1160, 1105, 1035, 960, 755

Ultraviolet Absorption Spectra:

| Solvent | λ Max in mμ, | log ε | |
|---|---|---|---|
| EtOH | 213 | 4.42 | |
|  | 236 | 4.45 | |
| EtOH | 257 sh | 4.31 | sh=shoulder |
|  | 279 | 4.31 | |
|  | 439 | 4.15 | |

EXAMPLE 2

7-Deoxysteffimycinone — U-25,920.

One gram of steffimycin is dissolved in methanol and 300 mg of 10% Pd on carbon is added. The mixture is shaken under hydrogen at an initial pressure of 45–50 psi for 93 hours. The mixture is filtered, and the solvent is removed from the filtrate by evaporation under reduced pressure. The residue is mixed with a mixture of water and methylene chloride. Some insoluble material is removed by filtration. The methylene chloride layer of the filtrate is removed, washed with water, then with a solution of ferric chloride in 1 N hydrochloric acid, and lastly with water again. The solvent is removed by evaporation under reduced pressure. The residue is chromatographed on 100 g of silica initially using methylene chloride-methanol (97:3) until about 180 fractions has been collected, followed by a mixture of the same solvents at a ratio of 9:1 and 1:1. Fractions 17–30 comprising the fastest moving fraction on TLC using a methylene chloride-methanol (97:3) solvent mixture are combined and evaporated to dryness under reduced pressure. The yield is 160 mg. of 7-deoxysteffimycinone. Recrystallization from methanol gives 85 mg. of 7-deoxysteffimycinone having a m.p. of 191°–194°C.

|  | C | H |
|---|---|---|
| Found | 63.09 | 4.67 |
| Calcd. for $C_{21}H_{18}O_8$ | 63.31 | 4.55 |

Infrared Absorption Spectra: (In a mineral oil mull). The following wave lengths are expressed in reciprocal centimeters: 3500, 1705, 1675, 1620, 1605 sh (shoulder), 1560, 1305, 1240, 1160, 1100, 965, 755

Ultraviolet Absorption Spectra:

| Solvent | λ Max in mμ | log ε | |
|---|---|---|---|
| EtOH | 213 | 4.41 | |
| | 236 | 4.45 | |
| | 258 sh | 4.29 | sh=shoulder |
| | 274 sh | 4.33 | |
| | 283 | 4.37 | |
| | 438 | 4.17 | |

EXAMPLE 3

Upon substituting steffimycin B for steffimycin in Example 1, there is obtained steffimycinone.

EXAMPLE 4

Upon substituting steffimycin B for steffimycin in Example 2, there is obtained 7-deoxysteffimycinone.

EXAMPLE 5

Upon substituting the 1 N methanolic hydrochloric acid in Example 1 with 0.1 to 3 N mineral acid selected from the group consisting of hydrochloric acid, sulfuric acid, and phosphoric acid, there is obtained steffimycinone.

EXAMPLE 6

Upon substituting steffimycin with steffimycin B in Example 1, and 1 N methanolic hydrochloric acid with 0.1 to 3 N mineral acid selected from the group consisting of hydrochloric acid, sulfuric acid, and phosphoric acid, there is obtained steffimycinone.

Steffimycinone and 7-deoxysteffimycinone have the following antibacterial activities as determined on a standard disc (6.35 mm.) plate assay. All organisms were run at 32° except for *M. avium* which was 37°. They were run for 16–18 hours.

*B. subtilis* medium
| | |
|---|---|
| Beef Extract | 0.15% |
| Yeast Extract | 0.3 % |
| Gelysate Peptone[1] | 0.6 % |
| Agar | 1.5 % |

[1]Obtained from BBL Division of Becton, Dickinson & Co., Cockeysville, Maryland 21030 U.S.A.

*S. lutea* and *B. cereus* medium
| | |
|---|---|
| Gelysate Peptone | 0.6 % |
| Trypticase Peptone[1] | 0.4 % |
| Yeast Extract | 0.3 % |
| Beef Extractives | 0.15% |
| Dextrose | 0.1 % |
| Agar | 1.5 % |

[1]Obtained from BBL Division of Becton, Dickinson & Co., Cockeysville, Maryland 21030 U.S.A.

*M. avium* medium
Brain and Heart Infusion Agar (All wts./liter)
| | |
|---|---|
| Calf Brains, infusion from | 200 g |
| Beef Hearts, infusion from | 250 g |
| Proteose Peptone, Difco | 10 g |
| Bacto - Dextrose | 2 g |
| NaCl | 5 g |
| $Na_2HPO_4$ | 2.5 g |
| Agar | 15 g |

*B. subtilis* synthetic medium
| | |
|---|---|
| $Na_2HPO_4 \cdot 7H_2O$ | 1.5 g/liter |
| $KH_2PO_4$ | 4.3 g/liter |
| $(NH_4)_2SO_4$ | 1.0 g/liter |
| $MgSO_4$ | 0.1 g/liter |
| Glucose | 2.0 g/liter |
| Agar | 15.0 g/liter |
| Distilled Water | 1 liter |
| Metallic ion stock solution[1] | 1 ml/liter |
| Final pH | 6.2 |

[1]Metallic ion stock solution
| Compound | Concentration |
|---|---|
| $NaMoO_4 \cdot 2H_2O$ | 200 mcg/ml |
| $CoCl_2$ | 100 mcg/ml |
| $CuSO_4$ | 100 mcg/ml |
| $MnSO_4$ | 2 mg/ml |
| $CaCl_2$ | 25 mg/ml |
| $FeCl_2 \cdot 4H_2O$ | 5 mg/ml |
| $ZnCl_2$* | 5 mg/ml |

*$ZnCl_2$ has to be dissolved separately using a drop of 0.1 N HCl for 10 ml of water.

| Antibiotic Tested | Organism | Zone Size (mm) |
|---|---|---|
| Steffimycinone: | *B. subtilis* (synthetic agar) | 22 |
| | *M. avium* | 17 |
| | *B. subtilis* | 15 |
| | *B. cereus* | 13 |
| 7-Deoxysteffimycinone: | *S. lutea* | 23 |
| | *M. avium* | 14 |

I claim:

1. Steffimycinone, a compound having the following structure:

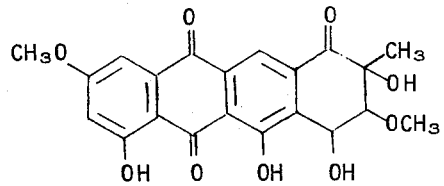

and non-toxic alkali and alkaline earth metal salts thereof.

2. 7-Deoxysteffimycinone, a compound having the following structure:

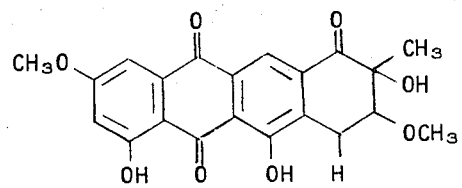

and non-toxic alkali and alkaline earth metal salts thereof.

3. 4,6,7-Tri-O-acylates of steffimycinone wherein said acyl group consists of hydrocarbon carboxylic acid acyl of from 2 to 18 carbon atoms, inclusive; halo-, nitro-, hydroxy-, amino-, cyano-, thiocyano-, and lower alkoxy-substituted hydrocarbon carboxylic acid acyl of from 2 to 18 carbon atoms, inclusive.

4. 4,6-Di-O-acylates of 7-deoxysteffimycinone wherein said acyl group consists of hydrocarbon carboxylic acid acyl of from 2 to 18 carbon atoms, inclusive; halo-, nitro-, hydroxy-, amino-, cyano-, thiocyano-, and lower alkoxy-substituted hydrocarbon carboxylic acid acyl of from 2 to 18 carbon atoms, inclusive.

* * * * *